(12) United States Patent
Hall et al.

(10) Patent No.: US 11,542,300 B2
(45) Date of Patent: *Jan. 3, 2023

(54) CHROMATOGRAPHIC METHODS FOR PURIFICATION OF PROTEINS FROM PLASMA

(71) Applicant: Cytiva BioProcess R&D AB, Uppsala (SE)

(72) Inventors: Martin Hall, Uppsala (SE); Karolina Busson, Uppsala (SE); Jean-Luc Maloisel, Uppsala (SE); Helena Skoglar, Uppsala (SE)

(73) Assignee: Cytiva BioProcess R&D AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/564,232

(22) PCT Filed: Apr. 4, 2016

(86) PCT No.: PCT/EP2016/057356
§ 371 (c)(1),
(2) Date: Oct. 4, 2017

(87) PCT Pub. No.: WO2016/162310
PCT Pub. Date: Oct. 13, 2016

(65) Prior Publication Data
US 2018/0127460 A1    May 10, 2018

(30) Foreign Application Priority Data
Apr. 10, 2015  (GB) .................... 1506117

(51) Int. Cl.
| | | |
|---|---|---|
| *C07K 1/18* | (2006.01) | |
| *B01J 41/20* | (2006.01) | |
| *B01D 15/36* | (2006.01) | |
| *B01D 15/38* | (2006.01) | |
| *A61K 38/36* | (2006.01) | |
| *A61K 38/48* | (2006.01) | |
| *A61K 35/16* | (2015.01) | |
| *C12N 9/64* | (2006.01) | |
| *B01D 15/34* | (2006.01) | |
| *C07K 14/47* | (2006.01) | |
| *C07K 14/755* | (2006.01) | |
| *C07K 14/765* | (2006.01) | |
| *C07K 16/00* | (2006.01) | |
| *A61K 38/00* | (2006.01) | |

(52) U.S. Cl.
CPC .............. *C07K 1/18* (2013.01); *A61K 35/16* (2013.01); *A61K 38/36* (2013.01); *A61K 38/4846* (2013.01); *B01D 15/34* (2013.01); *B01D 15/363* (2013.01); *B01D 15/3847* (2013.01); *B01J 41/20* (2013.01); *C07K 14/472* (2013.01); *C07K 14/755* (2013.01); *C07K 14/765* (2013.01); *C07K 16/00* (2013.01); *C12N 9/644* (2013.01); *C12N 9/6424* (2013.01); *C12Y 304/21022* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,721,572 A | 1/1988 | Jordan | |
| 5,457,181 A * | 10/1995 | Michalski | C12N 9/647 530/381 |
| 7,208,093 B2 | 4/2007 | Berg et al. | |
| 8,329,871 B2 | 12/2012 | Borgvall et al. | |
| 2008/0207878 A1 | 8/2008 | Michel et al. | |
| 2010/0305305 A1* | 12/2010 | Poulle | C07K 14/755 530/383 |
| 2011/0155668 A1* | 6/2011 | Glad | C07K 1/22 210/656 |
| 2012/0122179 A1 | 5/2012 | Perret et al. | |
| 2014/0154233 A1 | 6/2014 | Pham et al. | |
| 2016/0024180 A1 | 1/2016 | Schroeder | |

FOREIGN PATENT DOCUMENTS

| | | |
|---|---|---|
| CN | 102584983 A | 7/2012 |
| EP | 0 408 029 A1 | 7/1990 |
| EP | 0600480 A2 | 12/1993 |
| WO | 2008/135568 A1 | 11/2008 |
| WO | 2009/007451 A1 | 1/2009 |
| WO | 2009/131526 A1 | 10/2009 |
| WO | 2010/005364 A1 | 1/2010 |
| WO | WO2011102790 * | 8/2011 |
| WO | 2012/134381 A1 | 10/2012 |
| WO | 2014/085861 A1 | 6/2014 |

(Continued)

OTHER PUBLICATIONS

Darcy et al. Methods Mol Biol. 2011:681:369-82 (Year: 2011).*
GE Healthcare Life Sciences. Multimodal Chromatography Handbook 2013 (Year: 2013).*
Accession P00740. Jul. 21, 1986. (Year: 1986).*
PCT International Search Report and Written Opinion for PCT Application No. PCT/EP2016/057356 dated Jun. 27, 2016 (13 pages).
GB Search Report for GB Application No. 11506117.90 dated Jan. 19, 2016 (4 pages).

(Continued)

*Primary Examiner* — Christian L Fronda
(74) *Attorney, Agent, or Firm* — Eversheds Sutherland (US) LLP

(57) ABSTRACT

The present invention relates to the field of chromatography. More closely, the invention relates to a chromatographic method for purification of plasmaproteins, such as Factor VIII, von Willebrand factor and Factor IX. The chromatographic method is performed on a matrix comprising an inner porous core and outer porous lid surrounding said core.

16 Claims, 2 Drawing Sheets

(56) References Cited

FOREIGN PATENT DOCUMENTS

WO 2014/188313 A1 11/2014

OTHER PUBLICATIONS

Anonymous, "Simplified Purification During Vaccine Production," ip.com, 2013, pp. 1-10.
Poster #10, "Colloids and Surfaces in Biologicay and Biomaterials—A Symposium on Surface and Materials Chemistry," Uppsala, Sweden, Nov. 4-6, 2015 (70 pages).
Japanese Office Action for JP Application No. 2017-550147 dated Feb. 25, 2020 (10 pages with English translation).
Office Action for U.S. Appl. No. 15/564,224 dated Jun. 10, 2020 (14 pages).
Burnouf-Radasevich et al., "Chromatographic Preparation of a Therapeutic Highly Purified von Willebrand Factor Concentrate from Human Cryoprecipitate," Vox Sang, 1992, 62:1-11.
Chinese Office Action for CN Application No. 201680020792.6 dated Jul. 21, 2020 (37 pages, with English translation).
Jun et al., "Preliminary Research of Preparation of Highly Purified Human Plasma Factor IX with Conventional Chromatography," Pharmaceutical Biotechnology, 1999, 6(2):107-109 (English abstract).
Ribeiro et al., "Anion-Exchange Purification of Recombinant Factor IX from Cell Culture Supernatant Using Different Chromatography Supports," Journal of Chromatograph B, 2013, 938:111-118.
Zhu et al., Molecular Biology and Diseases, 1994 (15 pages).
PCT International Search Report and Written Opinion for PCT Application No. PCT/EP2016/057351 dated May 23, 2016 (10 pages).
GB Search Report for GB Application No. 1506113.8 dated Jan. 5, 2016 (5 pages).
Non-Final Office Action for U.S. Appl. No. 15/564,224 dated Jun. 7, 2021 (18 pages).
Ruggeri et al., "von Willebrand Factor," FASEB, 1983, vol. 7, pp. 308-316.

* cited by examiner

CHROMATOGRAPHIC METHODS FOR PURIFICATION OF PROTEINS FROM PLASMA

CROSS REFERENCE TO RELATED APPLICATIONS

This application claims the priority benefit of PCT/EP2016/057356 filed on Apr. 4, 2016 which claims priority benefit of Great Britain Application No. 1506117.9 filed Apr. 10, 2015. The entire contents of which are hereby incorporated by reference herein.

FIELD OF THE INVENTION

The present invention relates to the field of chromatography. More closely, the invention relates to a chromatographic method for purification of plasmaproteins, such as Factor VIII, von Willebrand factor and Factor IX. The chromatographic method is performed on a matrix comprising an inner porous core and outer porous lid surrounding said core.

BACKGROUND OF THE INVENTION

Blood contains different types of cells and molecules which are necessary for vital body functions, and is therefore collected for therapeutic purposes, eg for blood transfusions. However, it is possible to separate and prepare different fractions from blood, such as red blood cells or cell-free plasma, which enables a more directed therapeutic treatment of medical conditions. Several proteins in plasma can also be further isolated and used for specific therapeutic treatments, eg albumin is used to restore blood volume, immunoglobulins are used for immune deficiencies, and coagulation factors are used for blood coagulation disorders.

Plasma contains proteins of different function, different size, different amount, etc, so there are different methods for purification of the different plasma proteins. The purification processes are often designed to obtain several target proteins from one single starting pool of plasma. The processes typically involve precipitation or chromatography steps or a combination thereof. Chromatography is often used to increase the purity of the target protein and reduce the risk for detrimental side effects. Many plasma proteins exhibit very potent activities, and if present as contaminants, they can cause adverse reactions even at very low levels, when administered to patients.

Collected human plasma is stored frozen, and the initial step in a plasma protein purification process is thawing and pooling of plasma. When thawing at low temperatures, typically 1-6 degrees C., some plasma proteins precipitate and can be collected by eg centrifugation. The collected precipitate is called cryoprecipitate, and can be used as a source of eg coagulation Factor VIII (FVIII) and von Willebrand Factor (vWF). Most of the FVIII in plasma is present as a complex with the large vWF multimers, and the two proteins are therefore often co-purified. The remaining liquid after removal of the cryprecipitate is often referred to as cryodepleted plasma or cryosupernatant, and this can be used as a source of eg albumin, immunoglobulin G (IgG), coagulation Factor IX (FIX).

The purification of many plasma proteins can be challenging. This can depend on the presence of small amounts of contaminants with undesired but potent activity, or that the proteins sometimes lose their activity or gain unwanted activity. For example, the FVIII easily loses activity, and the known methods used for purification are not satisfactory in many respects. Thus, there is a need of improved methods which can be operated at conditions where the proteins retain their activity, in order to obtain plasma products in good yields.

SUMMARY OF THE INVENTION

The present invention provides chromatographic materials and methods for purification of plasma proteins, especially for human plasma applications. The chromatographic materials are capable of separations based on different principles, eg size and bind/elute. The method of the invention is especially suitable for purification of plasma samples which contain both large proteins (eg FVIII/vWF) and smaller proteins (HSA, IgG, FIX) of therapeutic interest.

Thus, the present invention provides a chromatographic method for purification of therapeutic proteins from plasma, comprising the following steps: loading plasma on a chromatography column packed with a resin comprising porous shell beads having an inner porous core and an outer porous shell, wherein the inner core is provided with anion exchange ligands and the shell is inactive (ie not provided with any ligands) and wherein the porosity of the lid and core does not allow entering of molecules larger than 500 kD, such as FIII/vWF, adsorbing Factor IX (FIX) on the anion exchange ligands in the core; collecting separated plasma proteins in the flow through; and eluting FIX from the ligands in the core. Adjustments of running and elution buffer in a chromatographic method are within the knowledge of the skilled person in the field and examples thereof are described in the experimental section below.

The anion exchange ligands may be any anion exchange ligands but are preferably selected from diethylaminoethyl (DEAE), quaternary aminoethyl (QAE) or quaternary ammonium (Q), most preferably he anion exchange ligands are Q-ligands.

In a preferred embodiment other plasma proteins besides FIX are collected in the flow through separated from each other by the sieving effect of the core and shell and comprise Factor VIII (FVIII) and von Willebrand factor (vWF), IgG, human serum albumin (HSA) and Complement C3. See the chromatogram in FIG. 1B below, describing peaks A, B and C.

In an alternative embodiment the loading of plasma is repeated 1-20 times, preferably 5-10 times, followed by running buffer to obtain a corresponding number of flow throughs (FT's), before the FIX is eluted from the ligands in the core. Each loading is followed by running buffer of about one column volume and a corresponding number of FT's as number of loadings are obtained. This is described more closely in FIGS. 1A-1B below.

In the alternative embodiment specific fractions of respective FT are pooled to obtain FVIII/vWF, IgG/HSA and C3 respectively. Thus, on one and the same chromatography column separated plasma fractions are obtained for FVIII/vWF, IgG/HSA, C3 and FIX.

Preferably the total shell bead (i.e. shell plus core) thickness is 40-100 μm in diameter, and the lid thickness is preferably 2-10 μm. The ligand concentration in the core is preferably 50-200 μmole/ml.

In a further embodiment the shell is provided with affinity ligands, hydrophobic interaction ligands, IMAC ligands, cation exchange ligands or multimodal ligands (or any ligands that reply on another separation principle than anion exchange ligands); and other plasma protein than FIX, such as FVIII/vWF, IgG, HSA, C3, are adsorbed on the ligands in the shell in the same step as FIX is adsorbed on the ligands in the core; and wherein plasma proteins are sequentially eluted from the ligands in the shell (FVIII/vWF and/or IgG, HSA, C3, depending on chosen type of ligand) and ligands in the core (FIX).

Preferably the ligands in the shell are ligands having immunoglobulin affinity, such as Protein A or G or variants thereof known in the art.

The porous material used in the method of the invention is preferably a sieving material, such as a gel filtration material commonly used for chromatography. The porous material in the inner core may have the same or different porosity as the porous material in the lid. The porous material is derived from a synthetic polymer material, such as styrene or styrene derivatives, divinylbenzene, acrylamides, acrylate esters, methacrylate esters, vinyl esters and vinylamides, or from a natural polymer material, such as carbohydrate material selected from agarose, agar, cellulose, dextran, chitosan, konjac, carrageenan, gellan and alginate. The preferred porous material is agarose.

The shell and core may be made of agarose of the same porosity but they may also be made of different porosity.

In a second aspect the invention relates to use of plasma protein(s) obtained from the above method for therapy. For example albumin is used to restore blood volume, immunoglobulins are used for immune deficiencies, and coagulation factors are used for blood coagulation disorders.

It is contemplated that the plasma proteins, especially FIX, may be used for therapy without further purification from contaminants, but with necessary adjustments for biocompatibility etc.

Absorbance 280 nm—solid line; conductivity—dotted line; pH—dashed line.

Figure 1A:
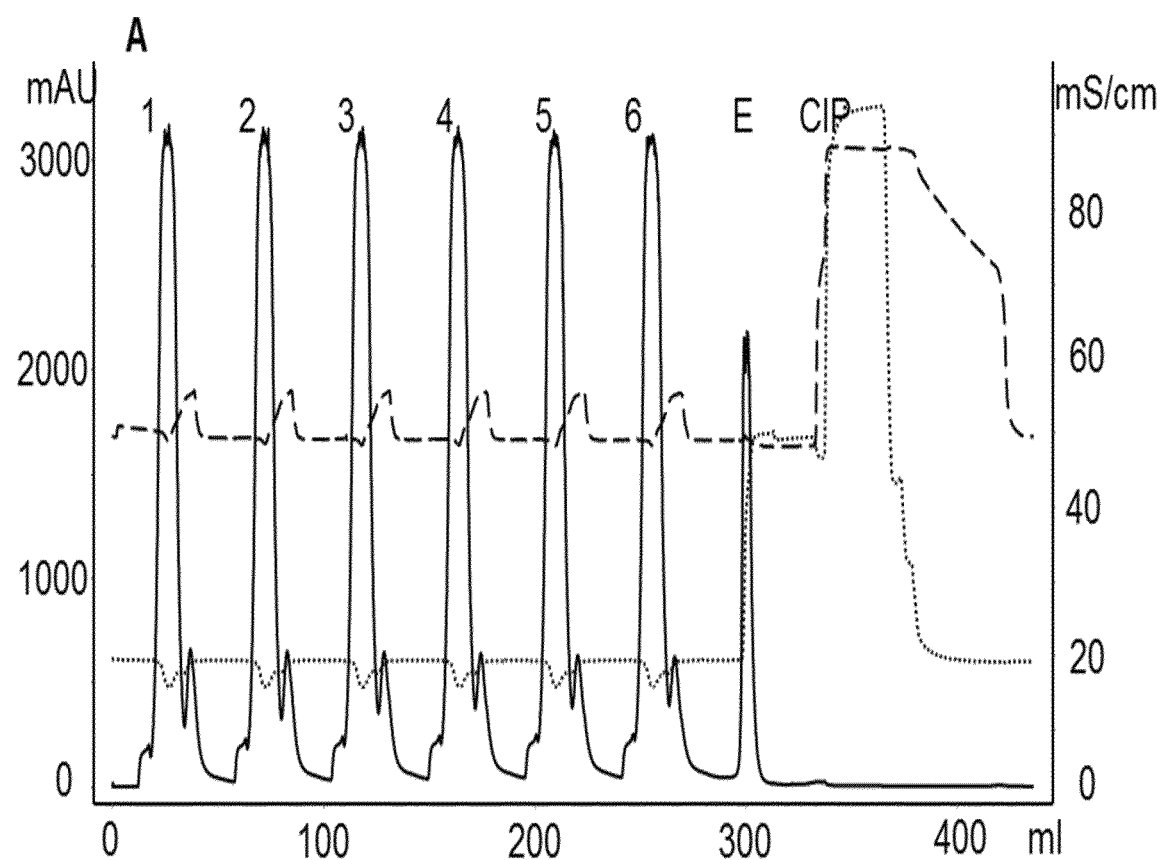
FIG. 1A: Chromatogram of plasma applied to prototype 99 column. Numbers 1-6=flow through (FT) peaks from the 6 sample applications; E=elution peak; CIP=cleaning-in-place.
Figure 1B:
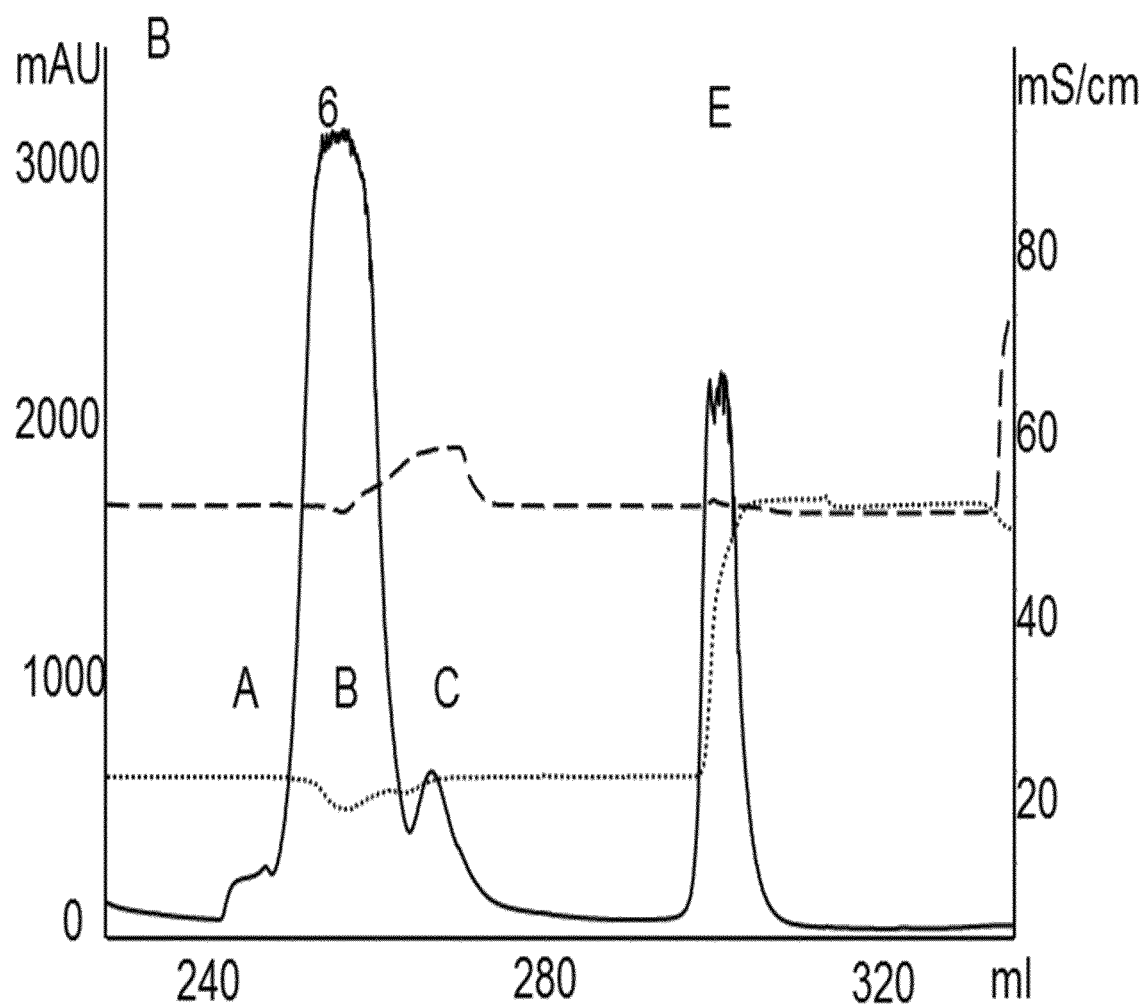

FIG. 1B: Partial enlargement of chromatogram of plasma applied to prototype 99 column according to FIG. 1A, showing final (6th) sample application and elution. 6=flow through peaks from the $6^{th}$ sample application; A=large molecules, eg FVIII/vWF; B=smaller molecules, eg albumin, IgG; C=partially retained material; E=eluted molecules, eg FIX.

Absorbance 280 nm—solid line; conductivity—dotted line; pH—dashed line.

DETAILED DESCRIPTION OF THE INVENTION

The invention will now be described more closely in connection with some non-limiting examples and the accompanying figures.

Example 1: Synthesis of Prototypes

General

Volumes of matrix refer to settled bed volume and weights of matrix given in gram refer to suction dry weight. For large scale reaction stirring is referring to a suspended, motor-driven stirrer since the use of magnet bar stirrer is prompt to damage the beads. Conventional methods were used for the analysis of the functionality and the determination of the degree of allylation, or the degree of ligand content on the beads.

Support Particles

The support particles used were highly crosslinked agarose beads, prepared according to the methods described in U.S. Pat. No. 6,602,990, which is hereby incorporated by reference in its entirety. The beads had a volume-weighted average diameter (D50, v) of 88 micrometers and a pore size distribution such that 69% of the pore volume was available to dextran molecules of Mw 110 kDa. This can also be expressed such that Kd for dextran 110 kDa on the beads was 0.69, when measured according to the methods described in "Handbook of Process Chromatography, A Guide to Optimization, Scale-Up and validation" (1997) Academic Press, San Diego. Gail Sofer & Lars Hagel eds. ISBN 0-12-654266-X, p. 368.

Allylation (Prototype 76)

250 mL (g) of of support particles were washed 6× gel volumes (GV) with distilled water, and then 3×GV with 50% NaOH. The gel was then sucked dry and transferred to a 2 L round bottom flask. 485 mL of 50% NaOH was added, mechanical propeller stirring was applied and the flask was immersed into a water bath at 50° C. After 30 minutes 80 mL of allyl glycidyl ether (AGE) was added. The reaction progressed for 18.5 h. The gel was washed 1×GV with distilled water, 3×GV with ethanol and then 8×GV with distilled water.

The allyl content, 276 µmol/mL, was measured by titration.

Prototype 99

Partial Bromination and Shell Inactivation 171.8 g of allylated gel slurry (prototype 76) was transferred to a glass filter (por. 2) and sucked dry. The dry gel is transferred to a 1000 mL round bottom flask fitted with a mechanical stirrer. 571 g of distilled water is added and the suspension is stirred at 300 rpm. 83.7 g of the 1.6% bromine solution is added during 1.5 min. After the addition the suspension is still white. The reaction proceeded for 15 min at rt. The round bottom flask was immersed in a bath and when the temperature had reached 50° C., 52 g of 50% NaOH was added. The reaction was let to stand for 17 hours. The reaction is transferred to a glass filter (por. 2) and washed with distilled water 10×1 GV. The remaining allyl content, 216 µmol/mL, was measured by titration. This corresponds to a theoretical shell thickness of 3.5 µm.

Core Bromination and Q Coupling 41.5 mL (g) of partial allylated base matrix from above was transferred drained to a 250 mL round bottom flask fitted with a mechanical stirrer. 10.37 g of distilled water and 1.66 g of sodium acetate was added. After stirring for a couple of minutes, 0.66 mL bromine is added with a pipette and the reaction is stirred at 300 rpm for additionally 20 min. Excess bromine is consumed by adding 4.15 mL of 40% sodium formate solution. The reaction is colourless. After 15 min, 8.30 mL of trimethyl ammonium chloride (TMAC) is added and the pH is adjusted to 11-11.5 by adding 50% NaOH. The reaction is stirred at 250 rpm at 30° C. for 18 h. The reaction is neutralized by adding 60% acetic acid to pH 5-7 before transferring to a glass filter (por. 3). The gel was washed with distilled water 10×1 GV, followed by 20% EtOH 2×1 GV. Titration of the ion exchange groups gave a Q ligand density of 125 µmol/ml.

Table 1 shows the lid thickness, ligand type and concentration in Prototype 99.

TABLE 1

| Resin | Lid thickness (μm) | Lid ligand (type, conc.) | Core ligand (type, conc.) |
|---|---|---|---|
| Prototype 99 | 3.5 | No ligand | Q, 125 μmol/ml |

Example 2: Chromatography of Plasma on Prototype 99

Sample

The sample was human plasma. Frozen human plasma was thawed and filtered through cotton, and applied to the column.

Buffers and Running Conditions

Column: Tricorn 10/300 with prototype 99, bed height 28.6 cm, column volume (CV) 22.5 mL.

Chromatography: Sample volume 6×5.2 mL (6×0.23 CV). Flow rate 50 cm/h (0.65 mL/min).

Running buffer: 20 mM Na-citrate, 0.15 M NaCl, 2.6 mM $CaCl_2$, pH 7.0.

Elution buffer: 20 mM Na-citrate, 0.5 M NaCl, 2.6 mM $CaCl_2$, pH 7.0.

Cleaning-in-place (CIP): 0.5 M NaOH.

The column was equilibrated with running buffer prior to the first sample application. 0.23 CV of plasma was applied to the column, followed by 1.8 CV of running buffer. This procedure, application of 0.23 CV of plasma followed by 1.8 CV of running buffer, was repeated 5 times, resulting in a total of 6 plasma sample applications. After the final 1.8 CV of running buffer, the column was eluted with 1.5 CV of high salt elution buffer. The column was then subjected to CIP by applying 1.5 CV of 0.5 M NaOH. Finally, the column was re-equilibrated by 4 CV of running buffer.

Analysis

Selected fractions were analyzed for FVIII activity (Chromogenix Coamatic Factor VIII kit), vWF (Technozym vWF: Ag ELISA kit), FIX (ROX Factor IX kit), and by SDS PAGE, and liquid chromatography-mass spectrometry (LC-MS).

The prototype 99 was packed in a Tricorn 10/300 column. The bed height was 28.6 cm (CV 22.5 mL) and the flow rate was 50 cm/h, to enable size-dependent group separation. The run consisted of 6 plasma sample applications (6×0.23 CV) resulting in 6 group separations, and one final high salt elution from the Q ligand in the core. The fractions from the 6 group separations were pooled so that one pooled fraction A with very large molecules, one pooled fraction B with smaller proteins, and one pooled fraction C with slightly retained smaller proteins, were obtained. The high salt elution resulted in one eluted fraction E. All fractions were analysed for FVIII, vWF and FIX. The chromatogram is shown in FIG. 1A and a partial enlargement is shown in FIG. 1B.

See Table 2 below for analytical results and yield calculations. The yields of FVIII and vWF in the fraction A pool was 37% and 40%, respectively. Fraction B and C pools had FVIII and vWF activities below level of quantification. The eluted fraction E contained 22% of the FVIII activity, and 13% of the vWF activity. This indicated that most of the large FVIII/vWF complexes do not enter the beads, and pass in the flow through, separated from the smaller molecules such as albumin and IgG in fraction B, which enter the beads but do not bind to the Q ligand in the core under these conditions. SDS PAGE and LC-MS showed that albumin and IgG were the main proteins in fraction B. LS-MC indicated that the major components in Fraction C were C3 and albumin. However, some FVIII/vWF complexes enter the pores and bind to the Q ligand, this could depend on the varying size of the FVIII/vWF complexes and the low flow rate. Fraction E consisted of molecules eluted with high salt, and it was the only fraction with FIX activity, 91% yield. This shows that the smaller FIX molecules enter the chromatography beads and bind to the Q ligand in the core. This demonstrates that by using a chromatography media with an inactive lid and ligand-containing core, it is possible to separate large (FVIII/vWF) and small (FIX) plasma proteins which both bind to the core ligand, as the large proteins are collected in the flow through, and the smaller molecules can be collected by elution.

TABLE 2

Plasma on prototype 99. FVIII, vWF and FIX activity. For fractions, see FIG. 1 A and B. X = not measured. LOQ = level of quantification (FVIII: 8 mU/mL, vWF: 0.10 U/mL, FIX: 30 mU/mL).

| Sample | Vol (mL) | FVIII (mU/mL) | FVIII (mU) | FVIII (%) | vWF (U/mL) | vWF (U) | vWF (%) | FIX (mU/mL) | FIX (mU) | FIX (%) |
|---|---|---|---|---|---|---|---|---|---|---|
| Plasma | 31.0 | 875 | 27125 | 100 | 1.00 | 31.0 | 100 | 1360 | 42160 | 100 |
| Fraction A | 35.7 | 280 | 9996 | 37 | 0.35 | 12.5 | 40 | <LOQ | | |
| Fraction B | 66.6 | <LOQ | | | <LOQ | | | <LOQ | | |
| Fraction C | 47.3 | <LOQ | | | <LOQ | | | <LOQ | | |
| Fraction E | 8.2 | 743 | 6093 | 22 | 0.49 | 4.0 | 13 | 4673 | 38319 | 91 |

The invention claimed is:

1. A chromatographic method comprising the following steps:
    loading plasma comprising plasma proteins on a chromatography column packed with a resin comprising porous lid beads having an inner porous core and an outer porous lid, wherein the inner core is provided with anion exchange ligands, and wherein the porosity of the lid and core does not allow entering of molecules larger than 500 kD;
    adsorbing Factor IX (FIX) on the anion exchange ligands in the core;
    collecting separated plasma proteins in the flow through; and
    eluting FIX from the ligands in the core.

2. The method of claim 1, wherein the anion exchange ligands are selected from diethylaminoethyl (DEAE), quaternary aminoethyl (QAE) or quaternary ammonium (Q).

3. The method of claim 2, wherein the anion exchange ligands are Q-ligands.

4. The method of claim 1, wherein other plasma proteins besides FIX are collected in the flow through separated from each other by the sieving effect of the core and shell and comprise Factor VIII (FVIII) and von Willebrand factor (vWF), IgG, human serum albumin (HSA) and Complement C3 (C3).

5. The method of claim 1, wherein the loading of plasma is repeated 1-20 times, followed by running buffer to obtain a corresponding number of flow throughs (FT's), before the FIX is eluted from the ligands in the core.

6. The method of claim 5, wherein other plasma proteins besides FIX are collected in the flow through separated from each other by the sieving effect of the core and shell and comprise Factor VIII (FVIII) and von Willebrand factor (vWF), IgG, human serum albumin (HSA) and Complement C3 (C3), and wherein specific fractions of respective FT are pooled to obtain FVIII/vWF, IgG/HSA and C3 respectively.

7. The method of claim 1, wherein the total lid bead thickness is 40-100 μm in diameter, and the lid thickness is 2-10 μm.

8. The method of claim 1, wherein the ligand concentration in the core is 50-200 μmol/ml.

9. The method of claim 1, wherein the lid is provided with affinity ligands, hydrophobic interaction ligands, IMAC ligands, cation exchange ligands or multimodal ligands; and at least one plasma protein other than FIX are adsorbed on the ligands in the lid in the same step as FIX is adsorbed on the ligands in the core; and wherein plasma proteins are sequentially eluted from the ligands in the lid and FIX is eluted from ligands in the core.

10. The method of claim 9, wherein the ligands in the lid are ligands having immunoglobulin affinity.

11. The method of claim 1, wherein the lid and core are made of agarose of the same porosity.

12. The method of claim 1, wherein the porosity of the lid is larger than of the core.

13. The method of claim 1, wherein the porosity of the lid is smaller than of the core.

14. The method of claim 5, wherein the loading of plasma is repeated 5-10 times.

15. The method of claim 9, wherein the at least one plasma protein other than FIX comprises FVIII/vWF, IgG, HSA, or C3.

16. The method of claim 1, wherein the lid is provided with ligands comprising at least one of Protein A or G or variants thereof.

* * * * *